(12) United States Patent
Milač et al.

(10) Patent No.: US 6,268,502 B1
(45) Date of Patent: Jul. 31, 2001

(54) PROCESS OF SYNTHESIS OF 5-METHOXY-2-[(4-METHOXY-3,5-DIMETHY-2-PYRIDYL)METHYL]SULFINY-1H-BENZIMIDAZOLE

(75) Inventors: Nataša Hafner Milač, Ljubljana; Darja Jereb, Radomlje, both of (SI)

(73) Assignee: LEK, Tovarna Farmacevtskih in Kemicnih Izdelkov. D.D., Ljubljana (SI)

( * ) Notice: Subject to any disclaimer, the term of this patent is extended or adjusted under 35 U.S.C. 154(b) by 0 days.

(21) Appl. No.: 09/463,651
(22) PCT Filed: Jul. 12, 1999
(86) PCT No.: PCT/SI99/00020
§ 371 Date: Aug. 30, 2000
§ 102(e) Date: Aug. 30, 2000
(87) PCT Pub. No.: WO00/02876
PCT Pub. Date: Jan. 20, 2000

(30) Foreign Application Priority Data

Jul. 13, 1998 (SI) ..................... 9800196

(51) Int. Cl.$^7$ ................. C07D 401/12
(52) U.S. Cl. ........................ 546/273.7
(58) Field of Search ..................... 546/273.7

(56) References Cited

U.S. PATENT DOCUMENTS

| | | |
|---|---|---|
| 4,255,431 | 3/1981 | Junggren et al. ............ 514/338 |
| 4,472,409 * | 9/1984 | Senn-Bilfinger ............ 546/273.7 |
| 4,689,333 * | 8/1987 | Nohara et al. ............ 514/338 |
| 5,386,032 | 1/1995 | Brändström ............ 514/338 |
| 5,958,955 * | 9/1999 | Gustavsson et al. ............ 514/338 |

FOREIGN PATENT DOCUMENTS

WO 98/28294  2/1998  (WO).
WO 99/08500  2/1999  (WO).

OTHER PUBLICATIONS

CA 109:149534, Binder et al., 1988.*

CA 108:186738, Matsuishi et al., 1988.*

* cited by examiner

*Primary Examiner*—Jane Fan
(74) *Attorney, Agent, or Firm*—Burns, Doane, Swecker & Mathis, LLP

(57) ABSTRACT

An improved process of synthesis of 5-methoxy-2-[(4-methoxy-3,5-dimethyl-2-pyridyl)methyl]sulfinyl-1H-benzimidazole (omeprazole) by oxidation of 5-methoxy-2-[[(4-methoxy-3,5-dimethyl-2-pyridyl)methyl]thio]benzimidazole with 3-chloroperoxy-benzoic acid in ethyl acetate wherein omeprazole is poorly soluble, at a temperature between −10° C. and 5° C. is disclosed. The second step is a purification of the crude product by dissolution and reprecipitation of the final product.

1 Claim, No Drawings

PROCESS OF SYNTHESIS OF 5-METHOXY-2-[(4-METHOXY-3,5-DIMETHY-2-PYRIDYL)METHYL]SULFINY-1H-BENZIMIDAZOLE

TECHNICAL FIELD (C07D 401/12)

The present invention relates to an improved process of synthesis of 5-methoxy-2-[(4-methoxy-3,5-dimethyl-2-pyridyl)methyl]sulfinyl- 1H-benzimidazole (omeprazole) of the formula

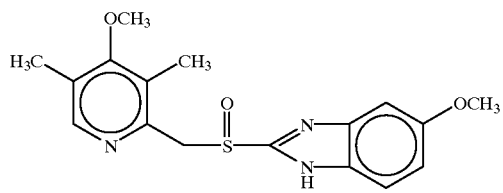

wherein 5-methoxy-2-[[(4-methoxy-3,5-dimethyl-2-pyridyl)methyl]thio]benzimidazole is reacted with 3-chloroperoxybenzoic acid in ethyl acetate, wherein the final product—omeprazole—is poorly soluble.

Omeprazole is the first medicament from the group of formulations for controlling the secretion of gastric acid, from the group of proton pump inhibitors. Namely, it inhibits the enzyme H/K-ATPase (a proton pump) in a parietal cell and thus also inhibits the last phase of acid secretion.

TECHNICAL PROBLEM

There is a constant need to prepare omeprazole of high purity in a simple and readily feasible way. In the literature processes of synthesis up to a crude omeprazole are disclosed; said omeprazole, however, contains by-products and hence it is not suitable for pharmaceutical use.

PRIOR ART 5-methoxy-2-[(4-methoxy-3,5-dimethyl-2-pyridyl)methyl]sulfinyl- 1H-benzimidazole (omeprazole) was disclosed for the first time in U.S. Pat. No. 4,255,431. In the process of preparing 2-(2-pyridylmethylsulfinyl) benzimidazole compounds there is mentioned an oxidation of corresponding 2-(2-pyridylmethylthio)benzimidazole compounds with 3-chloroperoxybenzoic acid in a chloroform solution under stirring and cooling at a temperature under 5° C. 3-chlorobenzoic acid formed is then filtered off, the filtrate is diluted with methylene chloride, washed with $Na_2CO_3$, dried with $Na_2SO_4$, evaporated in vacuo and the residue is crystallized under addition of $CH_3CN$. Since omeprazole is unstable in an acidic medium, the cooling of the reaction mixture to 5° C. is necessary to prevent a decomposition of the omeprazole formed.

In U.S. Pat. No. 5,386,032 an improved process of synthesis of omeprazole is disclosed, comprising an oxidation of 5-methoxy-2-[[(4-methoxy-3,5-dimethyl-2-pyridyl)-methyl]thio]benzimidazole with 3-chloroperoxybenzoic acid in a methylene chloride solution at a constant pH from 8.0 to 8.6, the pH being achieved either with an aqueous $KHCO_3$ solution or by titration with NaOH. There follow an extraction of the reaction mixture with an aqueous NaOH solution, a separation of the aqueous phase from the organic phase and crystallization of omeprazole by an addition of alkyl formate to the aqueous phase. The reaction must take place in a two-phase system (aqueous phase and organic phase) because of instability of omeprazole in acidic medium and, after a separation of both phases, a selective crystallization of omeprazole from an aqueous solution of sodium salt of omeprazole and sodium m-chlorobenzoate is necessary as well. A disadvantage of the said process is also the fact that the pH of the aqueous phase over the reaction mixture has to be carefully monitored during the whole process.

In U.S. Pat. No. 5,578,732 a synthesis of 2-(2-pyridylmethylsulfinyl)benzimidazole compounds comprising an oxidation of 2-(2-pyridylmethylthio)benzimidazole compound with hydrogen peroxide in the presence of vanadium compounds as a catalyst is disclosed.

The oxidation rate in the presence of the catalyst depends upon the amount of the catalyst. Thus the reaction time given in Examples is from one to eight hours. At a greater amount of the catalyst there is also a risk of contamination of the final product with heavy metals.

THE INVENTIVE SOLUTION

The object of the present invention is an improved process of synthesis of omeprazole, wherein the title compound is isolated with high purity in a simple and readily feasible way.

All hitherto known and disclosed processes of synthesis of omeprazole by oxidation of 5-methoxy-2-[[(4-methoxy-3,5-dimethyl-2-pyridyl)methyl]thio]benzimidazole with 3-chloroperoxybenzoic acid are carried out in solvents wherein the final product—omeprazole—is soluble and hence the removal of the solvent as well as a further crystallization up to the final product are necessary. The removal of the solvent may be carried out by evaporation at reduced pressure, whereat a decomposition of omeprazole takes place. In the present invention the oxidation is carried out in a solvent wherein omeprazole is poorly soluble.

3-chlorobenzoic acid formed in oxidation is, due to the instability of omeprazole in acidic medium, the cause of omeprazole decomposition and therefore it is absolutely necessary that the acid formed and the final product are in contact for as short a period of time as possible. In hitherto known processes this problem has been solved by filtration or a simultaneous removal of 3-chlorobenzoic acid formed in oxidation by extraction into the alkaline aqueous phase, whereas the omeprazole formed remained in the organic phase. The isolation of the final product from a two-phase system, alkaline aqueous phase—organic phase, requires several steps (extraction of 3-chlorobenzoic acid from the organic phase into the alkaline aqueous phase, extraction of omeprazole with NaOH into the aqueous phase under pH control and temperature control, separation of the organic and aqueous phases, crystallization of omeprazole under pH control and filtration of the final product), which means a more sophisticated technological process.

The object of the invention is thus an improved process of the synthesis of omeprazole, wherein the effect of the acidic medium on omeprazole decomposition is reduced in such a way that as a solvent in the oxidation of 5-methoxy-2-[[(4-methoxy-3,5-dimethyl-2-pyridyl)methyl]thio]benzimidazole with 3-chloroperoxybenzoic acid ethyl acetate is used wherein the final product—omeprazole—is poorly soluble since omeprazole formed during the reaction is crystallized and the acid formed remains in the ethyl acetate solution. Hence, for the final isolation of the product only one step is necessary, i.e. the filtration of the product. Therefore the present invention is, with regard to technological feasibility, essentially more simple, more economical and faster.

The first step in the improved synthesis of omeprazole is oxidation of 5-methoxy-2-[[(4-methoxy-3,5-dimethyl-2-pyridyl)methyl]thio]benzimidazole with 3-chloroperoxybenzoic acid in ethyl acetate wherein omeprazole is poorly soluble, at a temperature between −10° C. and 5° C. and in equimolar amounts of reactants. Crude omeprazole is obtained, which has to be additionally purified due to the presence of the by-product 5-methoxy-2- [[(4-methoxy-3,5-dimethylpyridin-2-ylmethylsulfinyl)- 1H-benz-imidazole N-oxide.

The second step in the improved synthesis of omeprazole is thus the removal of the by-product by dissolution and reprecipitation of the final product. The dissolution is carried out in an aqueous solution of methylamine, to which solution acetone is added and by the addition of an acid, the pH is adjusted to a value between 7 and 8. After dilution with water the crystals separated are filtered off, washed with water and dried in vacuo. The second step in the improved synthesis of omeprazole is carried out at room temperature.

The invention is illustrated, but in no way limited by the following Examples:

EXAMPLE 1

5-methoxy-2-[[(4-methoxy-3,5-dimethyl-2-pyridyl)methyl]thio]benzimidazole (10 g; 0.0304 mole) was suspended in ethyl acetate (100 ml) and cooled below 0° C. 3-chloroperoxybenzoic acid (5.25 g; 0.0304 mole) was added in such a manner that the temperature did not exceed 5° C. After completed addition it was left to crystallize for another half an hour at a temperature below 5° C. The product formed was filtered off, washed with ethyl acetate and dried in vacuo. Crude omeprazole (8.3 g; 79.1%) was obtained.

Crude omeprazole (5 g) was dissolved in water (20 ml) and 40% aqueous methylamine (4 ml). The clear solution was diluted with acetone (30 ml) and the pH was adjusted to 7 to 8 with 1N HCl. To the suspension formed, water (70 ml) was added. The crystals separated were filtered off, washed with water and dried in vacuo. Pure omeprazole (4.6 g; 92%) was obtained.

EXAMPLE 2

5-methoxy-2-[[(4-methoxy-3,5-dimethyl-2-pyridyl)methyl]thio]benzimidazole (10 g; 0.0304 mole) was suspended in ethyl acetate (100 ml) and cooled below 0° C. 3-chloroperoxybenzoic acid (5.25 g; 0.0304 mole) was added in such a manner that the temperature did not exceed 5° C. After the completed addition it was stirred for half an hour, the cooling was removed, a 4% sodium carbonate solution (40 ml) was added and it was stirred for another half an hour. The product was filtered off and washed with water. After drying in vacuo crude omeprazole (8.0 g; 76.2%) was obtained and it was purified according to the process disclosed in Example 1.

What is claimed is:

1. An improved process for preparing 5-methoxy-2-[(4-methoxy-3,5-dimethyl-2-pyridyl)methyl]-sulfinyl-1H-benzimidazole (omeprazole) of the formula

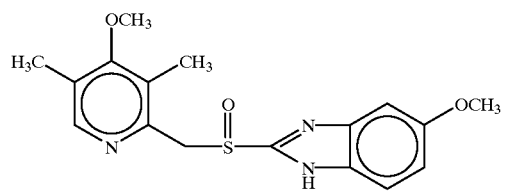

wherein the improvement is by reacting 5-methoxy-2-[(4-methoxy-3,5-dimethyl-2-pyridyl)methyl]-thio-1H-benzimidazole with 3-chloroperoxybezoic acid in ethyl acetate at a temperature between −10 C and 5 C and the product formed is purified by dissolution in an aqueous solution of methylamine, by precipitation under addition of hydrochloric acid up to pH between 7 and 8 and isolation of the title compound in a pure form.

* * * * *